(12) United States Patent
Karlovsky et al.

(10) Patent No.: US 10,433,736 B2
(45) Date of Patent: Oct. 8, 2019

(54) IMPLANTABLE VESSEL FLUID SENSOR

(71) Applicant: Infineon Technologies AG, Neubiberg (DE)

(72) Inventors: Kamil Karlovsky, Villach (AT); Bernhard Goller, Villach (AT); Dirk Hammerschmidt, Villach (AT); Horst Theuss, Wenzenbach (DE); Carsten von Koblinski, Villach (AT)

(73) Assignee: Infineon Technologies AG, Neubiberg (DE)

( * ) Notice: Subject to any disclaimer, the term of this patent is extended or adjusted under 35 U.S.C. 154(b) by 583 days.

(21) Appl. No.: 15/011,165

(22) Filed: Jan. 29, 2016

(65) Prior Publication Data
US 2016/0220125 A1     Aug. 4, 2016

(30) Foreign Application Priority Data
Jan. 30, 2015   (DE) .................. 10 2015 101 382

(51) Int. Cl.
| | | |
|---|---|---|
| *A61B 5/0215* | (2006.01) | |
| *A61B 5/022* | (2006.01) | |
| *A61B 5/00* | (2006.01) | |

(52) U.S. Cl.
CPC ............ *A61B 5/0215* (2013.01); *A61B 5/022* (2013.01); *A61B 5/6852* (2013.01)

(58) Field of Classification Search
CPC ...... A61B 5/0215; A61B 5/022; A61B 5/6852
USPC .................. 600/485, 486, 488, 505
See application file for complete search history.

(56) References Cited

U.S. PATENT DOCUMENTS

| | | | |
|---|---|---|---|
| 3,240,207 A | | 3/1966 | Barker et al. |
| 4,274,423 A | * | 6/1981 | Mizuno ................ A61B 5/0215 600/488 |
| 4,487,206 A | * | 12/1984 | Aagard ................ G01L 9/0077 600/342 |
| 4,803,992 A | * | 2/1989 | Lemelson .......... A61B 1/00096 600/342 |
| 4,886,070 A | * | 12/1989 | Demarest ........... A61B 5/02156 600/488 |
| 5,050,297 A | * | 9/1991 | Metzger ............... A61B 5/0215 29/825 |
| 5,795,325 A | * | 8/1998 | Valley .............. A61B 17/12022 604/103.1 |
| 5,814,016 A | * | 9/1998 | Valley .............. A61B 17/00234 604/96.01 |
| 5,879,499 A | * | 3/1999 | Corvi ................ A61M 25/0012 156/173 |
| 5,911,685 A | * | 6/1999 | Siess ................... F04D 29/0467 415/900 |

(Continued)

*Primary Examiner* — Navin Natnithithadha
(74) *Attorney, Agent, or Firm* — Murphy, Bilak & Homiller, PLLC

(57) ABSTRACT

An implantable vessel fluid sensor is configured to sense at least one vessel fluid parameter of a vessel. The implantable vessel fluid sensor includes a tubular body having a first end portion. The first end portion is configured to be inserted into and to form a sealed junction with an open vessel end of the vessel. The implantable vessel fluid sensor further includes a sensor unit connected to the tubular body. The sensor unit includes a sensor region configured to be in direct contact with the vessel fluid in a sealed junction state. A minimum distance between the sensor region and the first end portion is at most 10 times an outer diameter of the first end portion of the tubular body.

6 Claims, 13 Drawing Sheets

(56) References Cited

U.S. PATENT DOCUMENTS

| | | | | |
|---|---|---|---|---|
| 5,921,913 A * | 7/1999 | Siess | F04D 29/0467 | 600/16 |
| 5,964,694 A * | 10/1999 | Siess | H02K 5/08 | 415/900 |
| 6,454,720 B1 * | 9/2002 | Clerc | A61B 5/0002 | 600/481 |
| 6,855,115 B2 * | 2/2005 | Fonseca | A61B 5/0215 | 600/486 |
| 7,025,778 B2 * | 4/2006 | Hayashi | A61B 5/02014 | 623/1.16 |
| 7,147,604 B1 * | 12/2006 | Allen | A61B 5/0031 | 600/549 |
| 7,162,926 B1 * | 1/2007 | Guziak | A61B 5/0215 | 73/729.2 |
| 7,261,733 B1 * | 8/2007 | Brown | A61B 5/0028 | 623/1.34 |
| 7,340,288 B1 * | 3/2008 | Karicherla | A61B 5/0215 | 600/374 |
| 7,389,134 B1 * | 6/2008 | Karicherla | A61B 5/0215 | 600/375 |
| 7,399,313 B2 * | 7/2008 | Brown | A61B 5/0031 | 623/1.13 |
| 7,488,345 B2 * | 2/2009 | Brown | A61B 5/0028 | 623/1.23 |
| 8,303,511 B2 * | 11/2012 | Eigler | A61B 5/0215 | 600/481 |
| 9,241,638 B2 * | 1/2016 | Bornzin | A61B 5/0205 | |
| 9,949,692 B2 * | 4/2018 | Hunter | A61B 5/6862 | |
| 2003/0130581 A1 * | 7/2003 | Salo | A61N 1/056 | 600/485 |
| 2004/0138571 A1 * | 7/2004 | Salo | A61N 1/056 | 600/485 |
| 2004/0199238 A1 * | 10/2004 | Brown | A61B 5/0031 | 623/1.1 |
| 2005/0015014 A1 * | 1/2005 | Fonseca | A61B 5/0031 | 600/488 |
| 2005/0107866 A1 * | 5/2005 | Brown | A61B 5/0028 | 623/1.23 |
| 2006/0149347 A1 | 7/2006 | Hayashi et al. | | |
| 2006/0200220 A1 * | 9/2006 | Brown | A61B 5/0028 | 623/1.1 |
| 2007/0028698 A1 * | 2/2007 | Guziak | A61B 5/0215 | 73/729.2 |
| 2010/0041986 A1 * | 2/2010 | Nguyen | A61B 5/0066 | 600/427 |
| 2014/0276027 A1 * | 9/2014 | Gaddis | A61B 5/0215 | 600/427 |
| 2015/0335290 A1 * | 11/2015 | Hunter | A61F 2/07 | 623/1.13 |
| 2016/0317095 A1 * | 11/2016 | Berger | A61B 5/6862 | |
| 2017/0055850 A1 * | 3/2017 | Bogner | A61B 5/0476 | |

\* cited by examiner

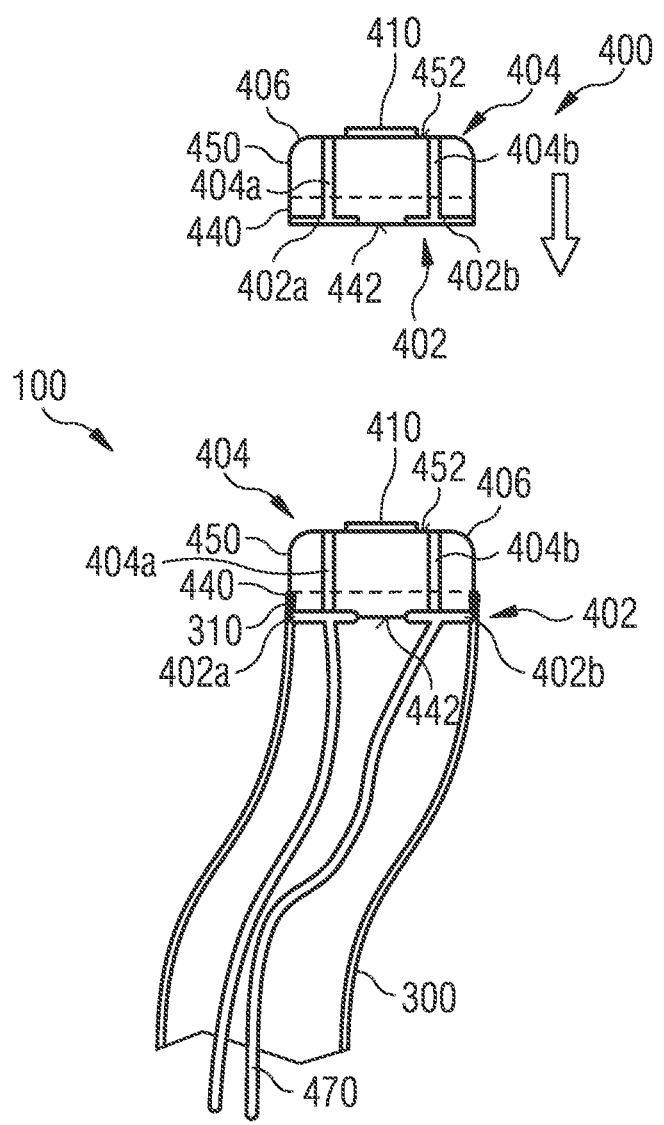

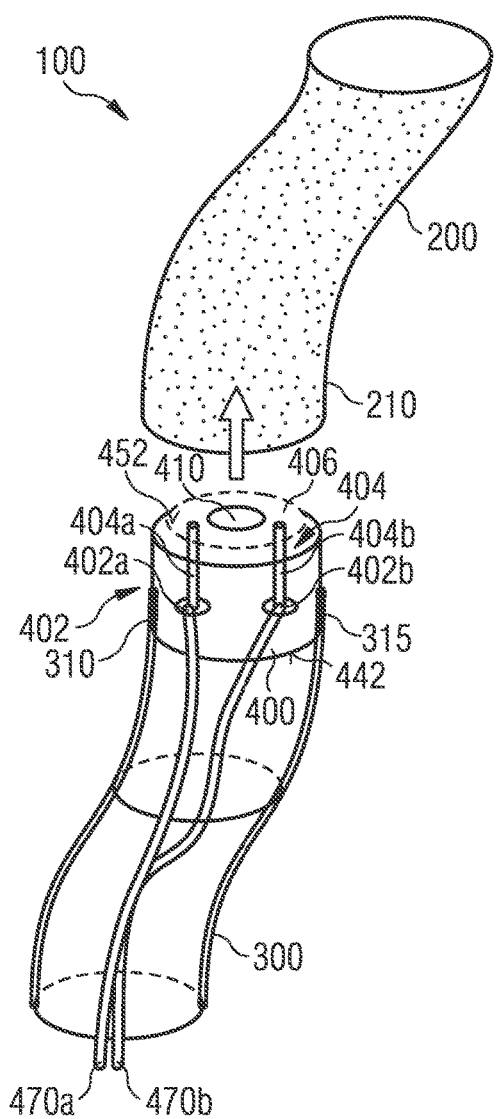
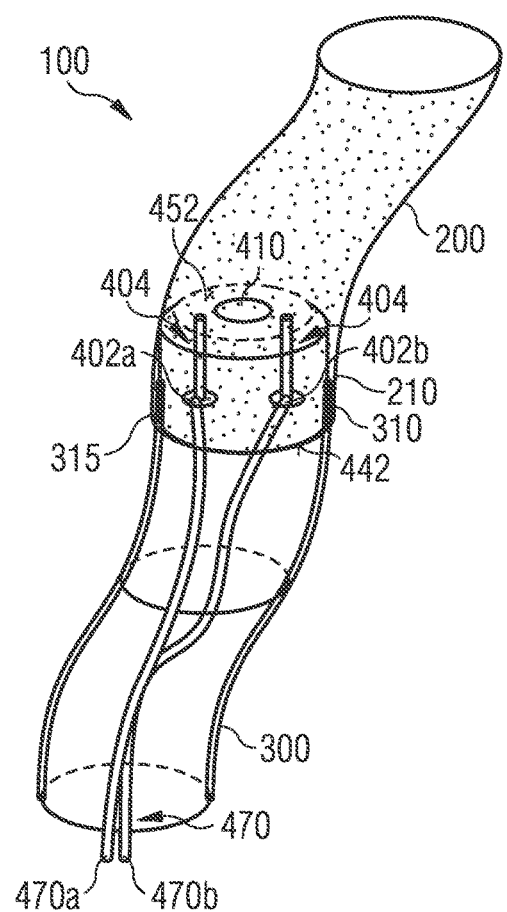

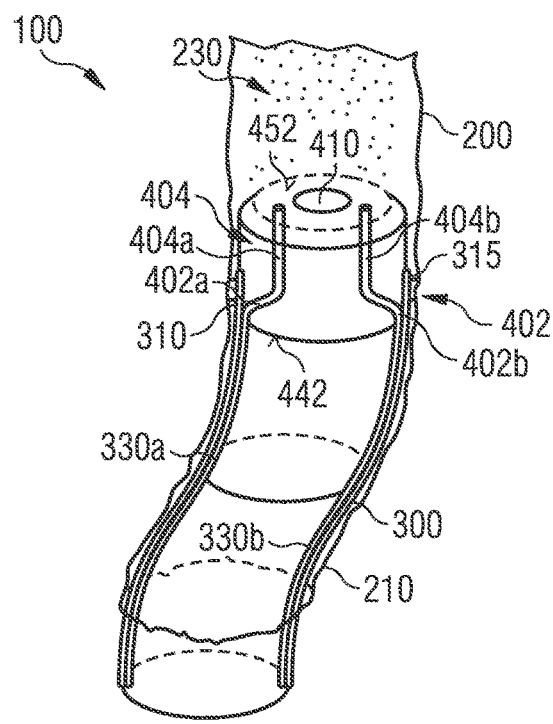
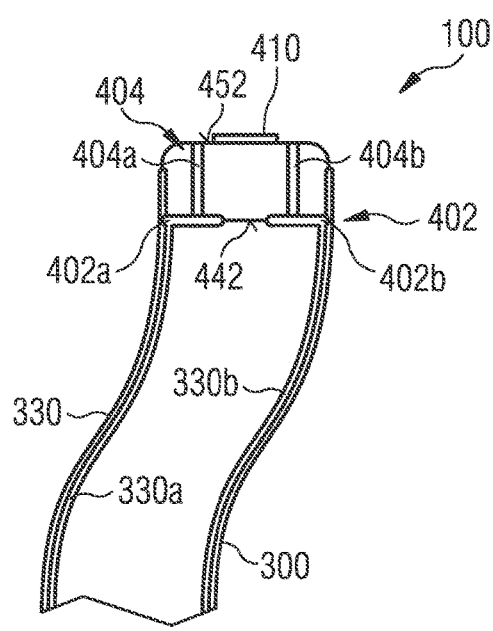
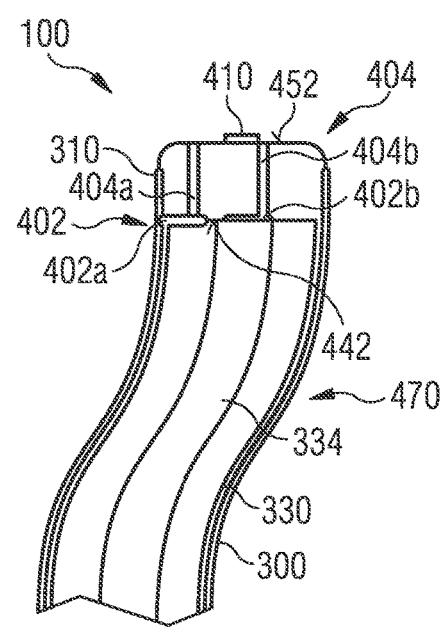

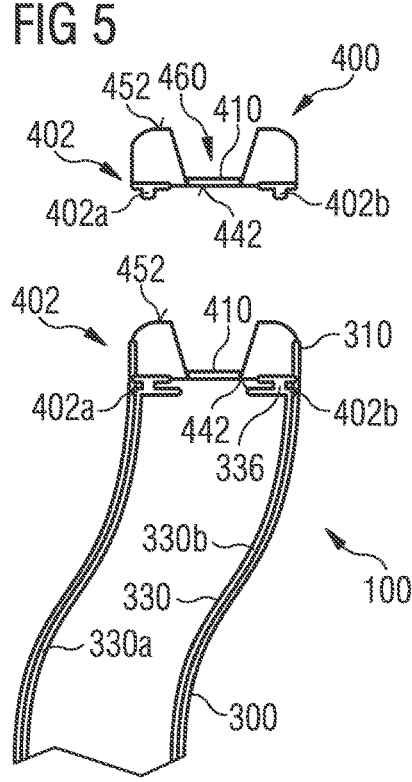
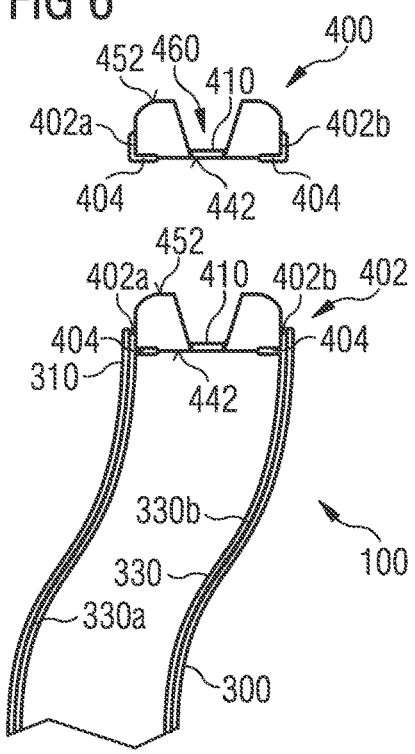
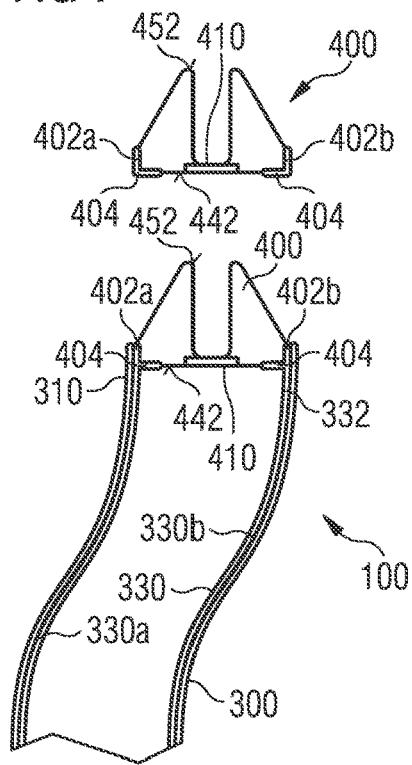
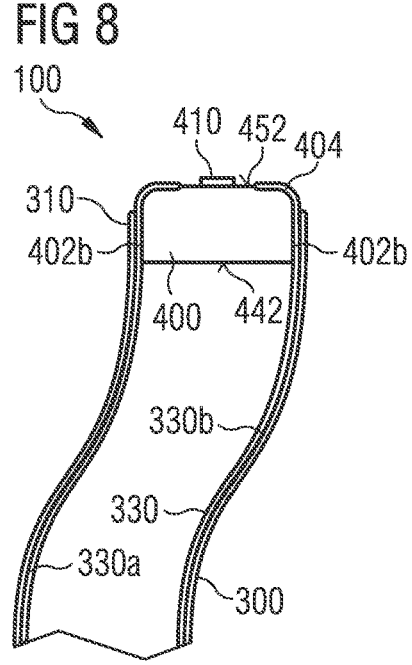

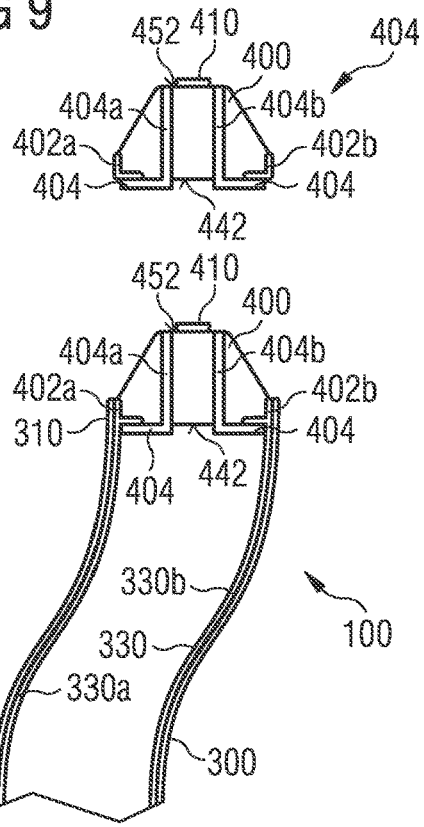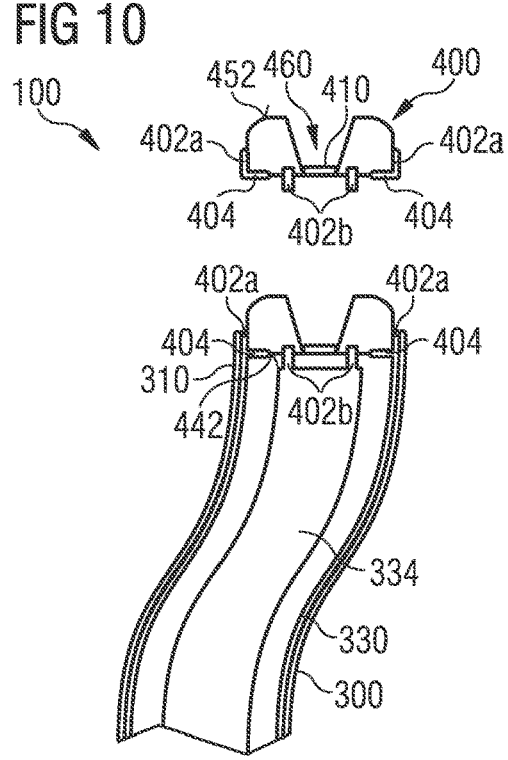

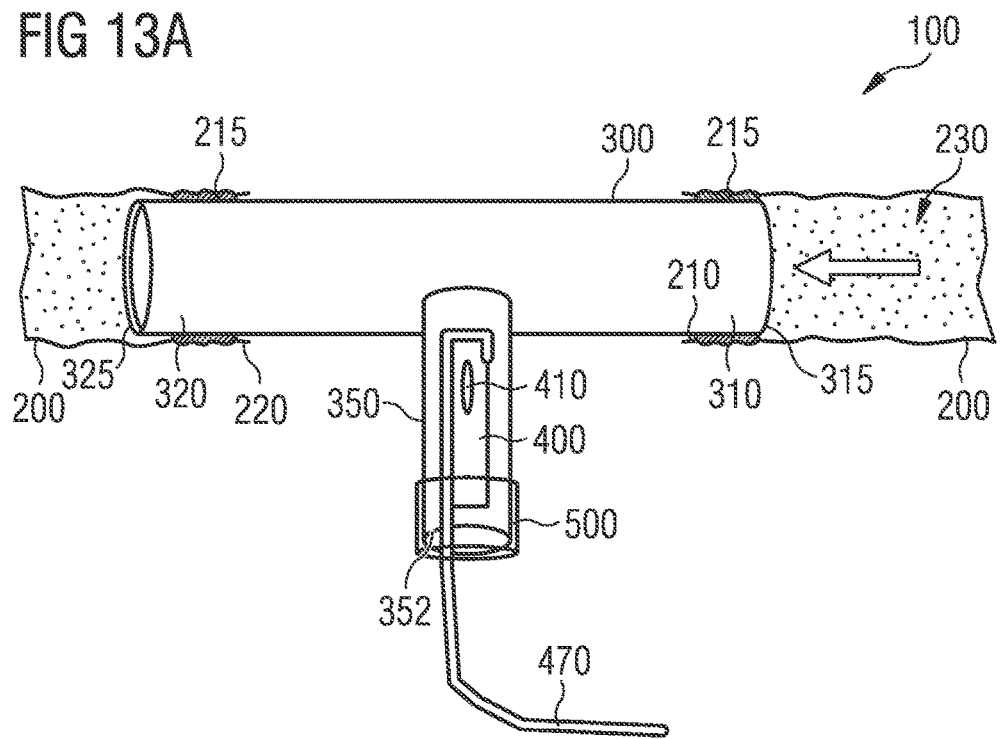
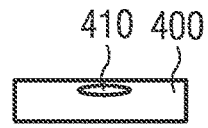

IMPLANTABLE VESSEL FLUID SENSOR

PRIORITY CLAIM

This application claims priority to German Patent Application No. 10 2015 101 382.7 filed on 30 Jan. 2015, the content of said application incorporated herein by reference in its entirety.

BACKGROUND

Vessel fluid sensors may be employed for blood pressure sensing of rodents such as laboratory mice in medical studies. At present, blood pressure sensing is performed with a catheter that is connected to an external measurement equipment. The catheter is fluid filled and transfers the pressure mechanically. However, the blood pressure is quite inaccurate, since the system of the catheter adds a fluid pillar to the pressure and depends on the mouse body as well as the ambient temperature. It further forms a mechanical low pass that limits the dynamic of the signals. In addition, the mouse is tied to the external catheter tube, which causes massive stress to the mouse and thus reduces the value of the measured data. Finally the mouse often dies when the catheter is removed.

There are transponders existing that combine the catheter measurement principle with a wireless data link to avoid the external tube that hinders the mouse from normal activity. Those transponders still represent a large handicap for the mouse since the volume of the transponder is about 2 cm$^3$ and thus occupies a volume in the small animal that impacts its normal anatomy. The measurement suffers from the same problems as the catheter since it also uses the fluid filled tube to transfer the pressure from the blood vessel to the pressure sensor inside the transponder capsule, but due to the shorter catheter length the effect should be limited. Furthermore, the battery powered RF transponder has a limited lifetime which is severely shorter than the live of the animal and it has to be explanted for refurbishing due to its high price.

It is an object to provide an implantable vessel fluid sensor providing an optimum pressure resolution and accuracy and being easy to implant.

SUMMARY

According to an embodiment of an implantable vessel fluid sensor, the implantable vessel fluid sensor is configured to sense at least one vessel fluid parameter of a vessel. The implantable vessel fluid sensor comprises a tubular body including a first end portion. The first end portion is configured to be inserted into and to form a sealed junction with an open vessel end of the vessel. The implantable vessel fluid sensor further comprises a sensor unit connected to the tubular body and comprising a sensor region configured to be in direct contact with the vessel fluid in a sealed junction state. A minimum distance between the sensor region and the first end portion is at most 10 times an outer diameter of the first end portion of the tubular body.

According to an embodiment of a method of implanting an implantable vessel fluid sensor, the method comprises: cutting a vessel into two parts, the two parts having an open vessel end and a remaining open vessel end, respectively; inserting the first end portion of the tubular body into the open vessel end; and forming a sealed junction between the first end portion and the open vessel end.

Those skilled in the art will recognize additional features and advantages upon reading the following detailed description and on viewing the accompanying drawings.

BRIEF DESCRIPTION OF THE DRAWINGS

The accompanying drawings are included to provide a further understanding of the invention and are incorporated in and constitute a part of this specification. The drawings illustrate the embodiments of the present invention and together with the description serve to explain principles of the invention. Other embodiments of the invention and intended advantages will be readily appreciated as they become better understood by reference to the following detailed description.

FIG. 2A is a schematic cross-sectional view of a sensor unit being assembled to form an implantable vessel fluid sensor according to an embodiment.

FIGS. 2B and 2C are schematic perspective views of an implantable vessel fluid sensor according to an embodiment before and after insertion into a vessel end.

FIG. 3 is a schematic perspective view of an implantable vessel fluid sensor being inserted into a vessel end according to an embodiment.

FIGS. 4A and 4B are schematic cross-sectional views of implantable vessel fluid sensors having a transmission line in a tubular body according to different embodiments.

FIGS. 5 to 7 are schematic cross-sectional views of sensor units and implantable vessel fluid sensors each having a backside fluid port according to different embodiments.

FIGS. 8 and 9 are schematic cross-sectional views of implantable vessel fluid sensors having shapes according to different embodiments.

FIG. 10 is a schematic cross-sectional view of an implantable vessel fluid sensor having a backside fluid port and a coaxial transmission line according to an embodiment.

FIG. 13A is a schematic side view of an implantable vessel fluid sensor having a first end portion and a second end portion and including a T-tube according to an embodiment.

FIG. 13B is a schematic side view of a sensor unit of an implantable vessel fluid sensor of FIG. 13A.

DETAILED DESCRIPTION

In the following detailed description, reference is made to the accompanying drawings, which form a part hereof, and in which are shown by way of illustrations specific embodiments in which the invention may be practiced. It is to be understood that other embodiments may be utilized and structural or logical changes may be made without departing from the scope of the present invention. For example, features illustrated or described for one embodiment can be used on or in conjunction with other embodiments to yield yet a further embodiment. It is intended that the present invention includes such modifications and variations. The examples are described using specific language which should not be construed as limiting the scope of the appending claims. The drawings are not scaled and are for illustrative purposes only. For clarity, the same elements have been designated by corresponding references in the different drawings if not stated otherwise.

The terms "having", "containing", "including", "comprising" and the like are open and the terms indicate the presence of stated structures, elements or features but not preclude additional elements or features. The articles "a", an and the are intended to include the plural as well as the singular, unless the context clearly indicates otherwise.

The term "electrically connected" describes a permanent low-ohmic connection between electrically connected elements, for example a direct contact between the concerned elements or a low-ohmic connection via a metal and/or highly doped semiconductor. The term "electrically coupled" includes that one or more intervening element(s) configured for signal transmission may be provided between the electrically coupled elements, for example resistors, resistive elements or elements that are controllable to temporarily provide a low-ohmic connection in a first state and a high-ohmic electric decoupling in a second state.

Figure 1A:
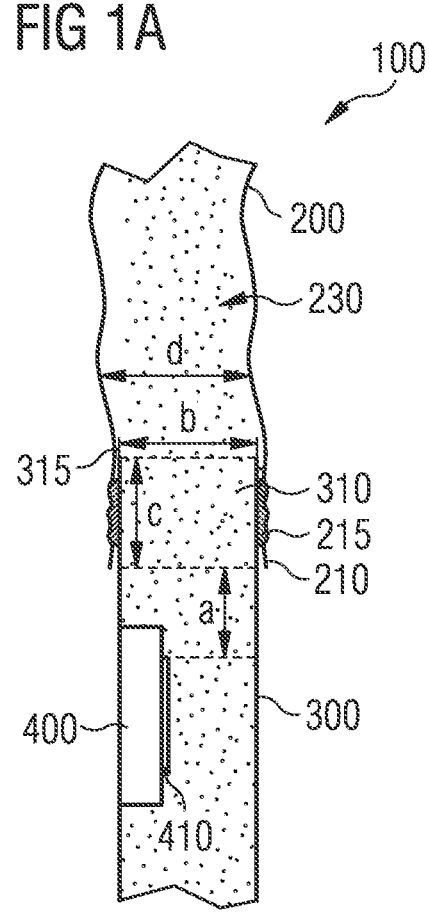
FIG. 1A is a schematic diagram of an implantable vessel fluid sensor according to an embodiment.

FIG. 1A is a schematic diagram of an implantable vessel fluid sensor 100 according to an embodiment.

The implantable vessel fluid sensor 100 is configured to sense at least one vessel fluid parameter of a vessel 200. The implantable vessel fluid sensor 100 comprises a tubular body 300 including a first end portion 310. The first end portion 310 is configured to be inserted into and to form a sealed junction 215 with an open vessel end 210 of the vessel 200. The implantable vessel fluid sensor 100 further comprises a sensor unit 400 connected to the tubular body 300. The sensor unit 400 comprises a sensor region 410 being configured to be in direct contact with the vessel fluid 230 in a sealed junction state. The minimum distance a between the sensor region 410 and the first end portion 310 is at most 10 times the outer diameter b of the first end portion 310 of the tubular body 300.

The first end portion 310 is a part of the tubular body 300, which is fully inserted in the vessel 200 in a sealed junction state. Thus, the first end portion 310 is a part of the tubular body state, which is extended from a first end 315 of the tubular body 300 to the open vessel end 210 of the vessel 200. The minimum distance a may be thus the distance between the open vessel end 210 of the vessel 200 and the part of the sensor region 410 being nearest to the open vessel end 210, as shown in FIG. 1A. In case the sensor unit 400 and the sensor region 410 are located at least partly inside the vessel 200, the minimum distance a between the sensor region 410 and the first end portion 310 is set to zero.

In any case, the first end portion 310 is a part of the tubular body 300, which is extended from the first end 315 to part being spaced from the first end 315 with a distance of the outer diameter b of the first end portion 310 of the tubular body 300. In other words, as can be seen from FIG. 1A, the first end portion 310 having a circular cylindric shape has a length c being equal to the outer diameter b of the tubular body 300. In case the opening area of the tubular body 300 at its first end 315 is not orthogonal to the length direction of the tubular body 300, but has an inclined surface, the length c of the first end portion 310 is measured from the first end 315, which is a part of the tubular body 200 being farthest to the open vessel end 210 in the sealed junction state. In other words, the first end 315 of the tubular body 200 is an end point of the first end portion 310 of the tubular body 200 in its length direction. In an embodiment, the minimum distance between the sensor region 410 and the first end 315 of the tubular body 300 may be at most 10 times, or 5 times, or 2 times the outer diameter b of the first end 315 of the tubular body 300. The minimum distance between the sensor region 410 and the first end 315 of the tubular body may be 100 mm, or 50 mm, or 10 mm, or 5 mm. In an embodiment, the minimum distance between the sensor unit 400 and the first end 315 of the tubular body may be 100 mm, or 50 mm, or 10 mm, or 5 mm.

The tubular body 300 may comprise a rigid or stiff material (having an elastic module of higher than 1 kN/mm$^2$) or a flexible material (having an elastic module of lower than 1 kN/mm$^2$). Furthermore, the first end portion 310 may comprise a different material than the remaining tubular body 300. The first end portion 310 may comprise, for example, a rigid material such as glass, metal (e.g. titanium), silicon, or a biocompatible material, wherein the remaining tubular body 300 may comprise a flexible material such as a synthetic material. The synthetic material may comprise PET, PI, or silicone.

The sealed junction between the open vessel end 210 and the first end portion 310 may be formed by clamping, by suture, or by tying. The sealed junction 215 may be formed by pressing the tissue of the vessel 200 against the outer wall of the tubular body 300 by a tie or by a clamping device. Herein, all methods for connecting an open vessel end 210 with a tubular body 300, which are known in the surgical field, shall be included for forming the sealed junction 215 between the first end portion 310 and the open vessel end 210.

The ratio of an outer diameter b of the first end portion 310 of the tubular body 300 and an inner diameter d of the non-dilated open vessel end 210 of the vessel 200 may be in a range of 0.5 to 2, or in a range of 0.8 to 1.5, or in a range of 1 to 1.2. The sealed junction 215 is essential in order to avoid a death of the animal such as a laboratory mouse during the implantation surgery and requires that the tubular body 300 has an outer diameter b that is at least slightly larger than the vessel 200 that hosts the tubular body 300. In case the sealed junction 215 is formed by clamping or tying, the outer diameter b of the first end portion 310 of the tubular body 300 may be also slightly smaller than the inner diameter of the open vessel end 210 of the vessel 200. On the other hand, the connection shall not expand the tissue of the vessel 200 too much in order to avoid an injury. Finally, the flexibility of the connection or the sealed junction 215 shall be high enough to avoid an annoyance of the animal.

The sensor unit 400 may be connected to the tubular body 300 by attaching or fixing the sensor unit 400 to an inner wall of the tubular body 300, e.g. by gluing. The sensor unit 400 may be connected to the tubular body 300 as shown in FIG. 1A. However, as can be seen from FIGS. 2A to 16, different ways of connecting the sensor unit 400 to the tubular body 300 may be provided. The sensor unit 400 may be a semiconductor device, in which the sensor region 410 is integrated. The sensor region 410 may, for example, a pressure sensing region of a semiconductor pressure sensor. One example of a semiconductor pressure sensor may be a MEMS-based pressure sensor integrated in a semiconductor die. In a MEMS-based pressure sensor, a polysilicon membrane covers a vacuum chamber in a semiconductor body, wherein the deflection of the polysilicon membrane relative to the semiconductor body may be measured positively by a piezo-electric effect.

The sensor unit 400 is a unit, which converts the at least one vessel fluid parameter of the vessel fluid being in direct contact with the sensor region 410 into an electrical or optical signal. The sensor region 410 may be integrated in the sensor unit 400. In an integrated state, the sensor region 410 is a part of the sensor unit 400. Thus, the minimum distance between the sensor unit 400, which converts the at least one vessel fluid parameter of the vessel fluid 230 into an electrical or optical signal, and the first end portion 310 may be at most 10 times the outer diameter b of the first end portion 310 of the tubular body 300. The sensor region 410 is the region, which is in direct contact to the vessel fluid 230. In case the at least one vessel fluid parameter is the vessel fluid pressure, the vessel fluid pressure of the vessel fluid is in direct contact with the sensor region 410 and directly converted into an electrical or optical signal by the sensor unit 400. The pressure signal is transferred from the sensor region 410 to the sensor unit 400 by a capacitive signal. The distance between the sensor region 410 and the sensor unit 400 may be below 100 µm, or below 50 µm, or below 10 µm. There is no fluid filled pipe transferring mechanically the fluid pressure to the sensor unit 400.

The vessel fluid may be blood. The vessel fluid may also be a lymph fluid. The at least one vessel fluid parameter may be a blood pressure or a lymph fluid pressure. The at least one vessel fluid parameter may also be a parameter of the blood fluid or lymph fluid related to a chemical composition of the respective fluid. The at least one vessel fluid parameter may thus comprise a blood sugar value, a blood heparin value, or an electrolyte content or concentration, respectively. The vessel 200 may be a carotid artery of a rodent. The rodent may be a mouse.

Figure 1B:
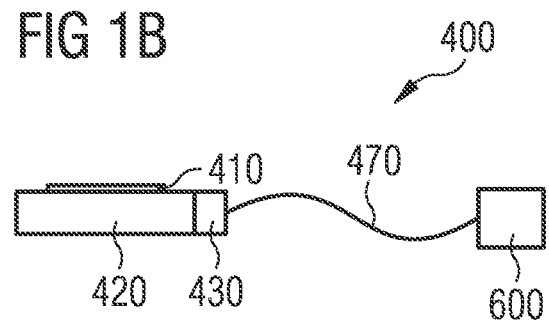
FIG. 1B is a schematic diagram of a sensor unit of an implantable vessel fluid sensor according to an embodiment, which is connected to an external device.

As shown in FIG. 1B, the sensor unit 400 may comprise a sensor part 420 configured to be in direct contact with the vessel fluid 230 in a sealed junction state to measure the at least one vessel fluid parameter, and a communication part 430 to transmit sensor data of the sensor part 420 to an external device 600. The sensor part 420 may include the sensor region 410 integrated as described above. The communication part 430 may be configured to convert the electrical or optical signal of the sensor part 420 into a digital signal. The communication between the communication part 430 and the external device 600 may be wireless. The communication between the communication part 430 and the external device 600 may also be performed via a transmission line 470. The transmission line 470 may be a micro wire comprising at least one electrical line. The external device 600 may also be directly connected to the sensor part 420 for transmitting an analogue sensor signal, without conversion of the analogue sensor signal in the communication part 430. The communication part 430 may also be configured to convert the optical or electrical signal of the sensor part 420 into a digital optical signal, which is transmitted to the external device 600 via the transmission line 470 being an optical fibre.

The external device 600 may be located at an outside portion of the animal. The external device 600 may also implanted in the animal, wherein the communication is performed wirelessly. In this case, the electric energy of the external device 600 being implanted in the animal may be supplied by an inductive coupling device. Thus, the implantable vessel fluid sensor 100 is inserted into the vessel 200 to provide an optimum pressure resolution and accuracy, wherein the lifetime problem of the sensor device is solved by recharging the battery of the external device 600 in a short operation cycle via an inductive link.

FIG. 2A is a schematic cross-sectional view of a sensor unit 400 being assembled to an implantable vessel fluid sensor 100 according to an embodiment.

As can be seen from FIG. 2A, the sensor unit 400 may be a semiconductor device, which comprises a proximal part 440 plugging the first end portion 310 of the tubular body 300 and having an interconnection side 442, and a distal part 450 protruding from the first end portion 310 of the tubular body 300 and having a sensor side 452.

The sensor unit 400 may be configured to measure at least one vessel fluid parameter of a vessel 200. In the following, an embodiment of the sensor unit 400 comprising a sensor region 410 being configured to measure a blood pressure will be described. The implantable vessel fluid sensor 100 allows an accurate monitoring of a blood pressure of a lab mouse with a sampling rate that allows to monitor the blood pressure transient over the heartbeat cycle instead of measuring just an average. Therefore, the micro-machined semiconductor pressure sensor of the sensor unit 400 is directly in contact with the vessel fluid 230 instead of using pressure sensors connected to the vessel 200 via a fluid filled tube of at least a few centimeter length.

For assembling the implantable vessel fluid sensor 100, the sensor unit 400 is inserted into the first end portion 310 of the tubular body 300. In addition, the transmission line 470 is guided through the tubular body 300 to the interconnection side 442 and connected to the sensor unit 400 via a contact structure 402 located on the interconnection side 442 of the sensor unit 400. The electrical connection to the sensor region 410 is provided by a connection structure 404. As shown in FIG. 2A, the connection structure 404 comprises through silicon vias 404a and 404b (TSVs), i.e. metallized holes in the semiconductor chip of the sensor unit 400, which are connected to the contact structure 402 on the interconnection side 442 of the sensor unit 400. The body of the sensor unit 400 may be a semiconductor die having the sensor region 410 including a pressure cell at the sensor side 452.

As shown in FIGS. 2B and 2C, the implantable vessel fluid sensor 100 may be inserted into the open vessel end 210, wherein the open vessel end 210 is sealed by the implantable vessel fluid sensor 100 plugging the vessel 200 without further clamping or tying. If necessary, the vessel 200 may be sealed by additional surgical measures as by clamping or tying.

Instead of transferring the blood pressure of the vessel 200 through a tube filled with a pressure transferring fluid to another location, where it is measured, the sensor unit 400 can be directly implanted into the vessel 200 and only transfer of the electrical signal to an electrical analysis system of the external device 600 is required.

The implantable vessel fluid sensor 100 is shaped in a geometry which simplifies the implantation into the vessel 200 as well as the forming of a sealed junction 215 (cf. FIG. 1A). In order to simplify the implantation process, the sensor unit 400 comprising the semiconductor die may have a circular shape along a cross-sectional area at the distal part 450 or at the first end portion 310 of the tubular body 300.

Furthermore, the sensor unit 400 may have rounded edges 406 at the distal part 450. The rounded edges 406 may be manufactured by depositing a photoresist onto the sensor side 452 of the semiconductor body of the sensor unit 400 (excluding the sensor region 410 comprising an active pressure sensing area) and partly removing the material at the edge 406, e.g. by variation of the development process. Thereafter, material is partly removed from the edge 406 of the semiconductor body of the sensor unit 400 using appropriate plasma treatments, e.g. with varying mask diameters.

The electrical or optical pressure signal is guided to the external device 600 through the tubular body 300 by the transmission line 470. For guiding the pressure signal, at least two electrical lines are necessary. As shown in FIGS. 2B and 2C, two separate isolated cables 470a and 470b may be connected to contact pads 402a and 402b of the contact structure 402 of the sensor unit 400.

As shown in FIG. 2C, a sensor die of the sensor unit 400 with a pressure cell of the sensor region 410 is provided, wherein the sensor die of the sensor unit 400 has rounded edges and through silicon vias 404a and 404b with contact pads 402a and 402b for electrical interconnects are provided to be connected with a round cable the external surface of which is out of biocompatible material. The electrical interconnects may be provided by at least two electrically isolated wires within the cable of the tubular body 300. The seal of the vessel 200 is provided by the cable module of the tubular body 300.

FIG. 3 is a schematic perspective view of an implantable vessel fluid sensor 100 being inserted into the open vessel end 210 according to an embodiment. As shown in FIG. 3, the tubular body 300 comprises at the inner side thereof a patterned wiring layer 330 comprising two wiring layer areas 300a and 300b electrically isolated from each other and being electrically coupled to the sensor region 410 of the sensor unit 400.

As shown in FIGS. 4A and 4B, the transmission line 470 comprises the patterned wiring layer 330, which comprises two electrically isolated wiring layer areas 330a and 330b. The wiring layer areas 330a and 330b are connected to contact pads 402a and 402b of the contact structure 402, respectively. The separate wiring layer areas 330a, 330b may then be connected to the sensor region 410 via the connection structure 404 comprising through silicon vias 404a and 404b, respectively.

As shown in FIG. 4B, a contiguous wiring layer 330 having only one wiring layer area 300a at the inner side of the tubular body 300 may be provided. The contiguous wiring layer 330 of FIG. 4B is then connected to contact pad 402a of the contact structure 402 and connected to the sensor region 410 via the connection structure 404. In addition, an inner wiring structure 334 may be provided, which is connected to the sensor region 410 via the connection structure 404. The inner wiring structure 334 and the contiguous wiring layer 330 form a coax cable structure inside the tubular body 300.

Thus, as can be seen from FIG. 2B to 4B, the tubular body 300 may either carry individual small cables within the circle-shaped tubular body 300, or use selective metallizations inside or outside the tubular body 300, or exhibit a multilayer shape out of dielectric material with selective metallizations in between the layers, for example a coax/triax cable or shielded cable or similar to a coax-cable. As shown in FIGS. 3 and 4A, an embodiment with electrical interconnects of the wiring layer areas 300a and 300b by selective metallization inside of the cable-tube of the tubular body 300 is provided. As shown in FIG. 4B, an embodiment with electrical interconnects by an coaxial cable is provided.

The outer surface of the sensor unit 400/tubular body 300—system may be of a biocompatible material. If necessary, the surfaces may also be coated with a respective biocompatible material, e.g. Parylene. According to another embodiment, the sensor unit 400 may have a different diameter than the tubular body 300 (which may be a silicone tube). This may be useful to gain freedom to control the flexibility of the connection independently of the diameter that is required to seal the vessel 200 e.g. the carotid artery of a rodent.

FIGS. 5 to 7 are schematic cross-sectional views of sensor units 400 and implantable vessel fluid sensors 100 each having a backside fluid port 460 according to different embodiments.

As can be seen from FIGS. 5 to 7, the sensor region 410 is arranged at the interconnection side 442 while being configured to in direct contact with the vessel fluid via a backside fluid port 460 at the sensor side 452.

As can be seen from FIG. 5, the sensor unit 400 comprises the sensor region 410 in the proximal part 440 of the sensor unit 400, which is the side of the semiconductor device of the sensor unit 400, on which the contact pads 402a and 402b of the contact structure 402 are arranged. Thus, the sensor region 410 and the contact pads 402a, 402b are on the same side, i.e. the interconnection side 442. In other words, the sensor unit 400 is interconnected with the patterned wiring layer 330 of the transmission line 470 in a flip-chip-interconnection manner instead of having through silicon vias 404a, 404b as shown in FIG. 2A to 4B. The contact side of the sensor region 410 is on the sensor side 452 being opposite to the interconnection side 442, wherein the direct contact of the sensor region 410 with the vessel fluid 230 is provided by the backside fluid port 460. The connection between the contact pads 402a, 402b and the patterned wiring layer 330 is formed by a wiring layer contact structure 336, on which the sensor unit 400 is arranged and the contact pads 402a, 402b are brought in contact with the wiring layer contact structure 336 in a flip-chip-manner by soldering or bonding. Thus, as shown in FIG. 5, flip-chip-like-contacts of the contact pads 402a and 402b on the active side of the chip of the sensor unit 400 are formed. This option requires a sensor cell of the sensor region 410, which is accessible by the pressure signal from the opposite side, i.e. the sensor side 452 of the sensor die of the sensor unit 400. As shown in FIG. 5, flip-chip-interconnects are provided instead of through silicon vias, which are suitable for pressure sensor chips acting as sensor units 400 with backside fluid port 460.

As shown in FIG. 6, the contact pads 402a, 402b of the contact structure 402 may also be arranged on the side portion of the proximal part 440 of the sensor unit 400 to be in contact with the patterned wiring layer 330 on the inner side of the tubular body 300. Herein, an connection structure 404 is in contact with the contact pads 402a, 402b of the contact structure 402 to be in contact with the sensor region 410 of the sensor unit 400. As shown in FIG. 6, an embodiment with electrical chip contacts at the sidewall of the sensor die is provided.

In the sensor unit structure as shown in FIG. 5 and FIG. 6, only the contact structure 402, the connection structure 404, and the sensor region 410 may be provided to minimize the size of the sensor unit 400. However, further logical electronic structures may be integrated in the sensor unit 400 for converting the capacitive signal of the sensor region 410 measuring the pressure of the vessel fluid 230 into an amplified analogue signal or a digital signal.

As shown in FIG. 7, the distal part 450 of the sensor unit 400 may be cone-shaped, to simplify the injection of the implantable vessel fluid sensor 100 into the open vessel end 210 of the vessel 200. As shown in FIG. 7, an embodiment with a cone-shape chip geometry is provided to facilitate the implantation into the vessel 200.

As further shown in FIG. 8, the sensor unit 400 may also be brought in contact with the patterned wiring layer 330 of the tubular body 300 via contact pads 402a, 402b located at a side portion of the proximal part 440 and the distal part 450, wherein the sensor region 410 is located at the sensor side 452. Herein, the patterned wiring layer 330 is separated into at least two electrically isolated wiring layer areas 330a and 330b on the inner side of the tubular body 300 and in contact with a respective contact pad 402a and 402b, as shown in FIGS. 6 to 8. As shown in FIG. 8, an embodiment with electrical interconnects is provided, e.g. by selective metallization inside of the cable-tube of the tubular body 300.

As shown in FIG. 9, a combination of through silicon vias 404a and 404b, an connection structure 404 being on the interconnection side 442 and a contact structure 402 being arranged at a side portion of the proximal part 440 may be combined. In this structure, the distal part 450 of the sensor unit 400 is cone-shaped, wherein the sensor region 410 is located at the sensor side 452.

As shown in FIG. 10, a structure of the implantable vessel fluid sensor 100 as shown in FIG. 6 may be combined with an inner wiring structure 334 to form a coaxial interconnection line structure. In this case, the contiguous wiring layer 330 is formed continuously on the inner side of the tubular body 300 to form a coaxial line structure. In addition, the inner wiring structure 334 may be isolated or the surface of the contiguous wiring layer 330 may be isolated, e.g. by a resin or a silicone layer, to prevent a shunt between the contiguous wiring layer 330 and the inner wiring structure 334. The structure of FIG. 10 includes contact pads 402a on the proximal part 440 of the sensor unit 400, which are arranged continuously at the sidewall of the sensor die of the sensor unit 400, to form a contact with the contiguous wiring layer 330. Further, contact pads 402b are provided at the interconnection side 442 to form a contact with the inner wiring structure 334. Thus, metal conductor lines of the contact pads 402a, e.g. as shown in the flip-chip-option of FIG. 5, or in the standard configuration as shown in FIG. 8, may be used to form a contact between the sensor unit 400 and the electrical connection structure of the tubular body 300. As shown in FIG. 10, an embodiment with electrical chip contacts acting as contact pad 402a are provided at the sidewall of the sensor die of the sensor unit 400 and a coaxial cable is further provided.

Figure 11A:
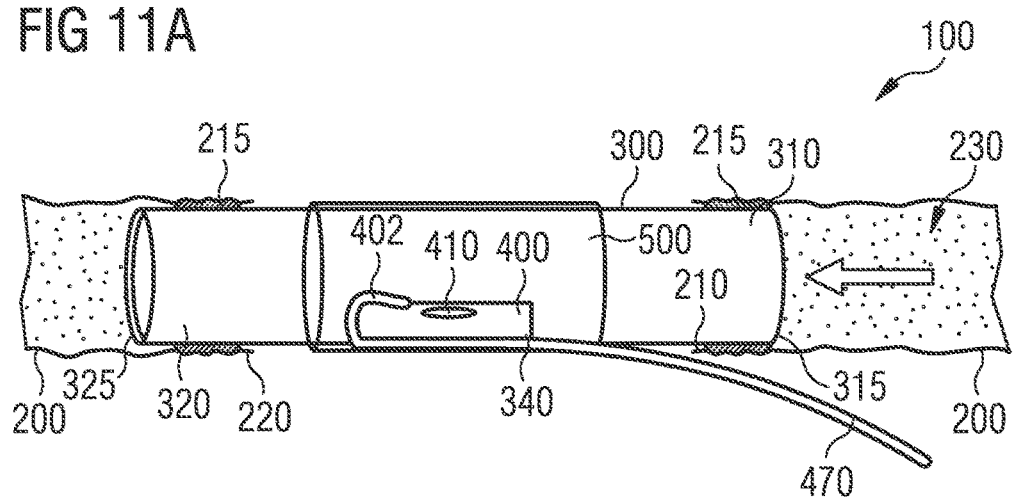
FIGS. 11A and 11B are a schematic side view and a schematic top view of an implantable vessel fluid sensor having a first end portion and a second end portion according to an embodiment, respectively.
Figure 11B:
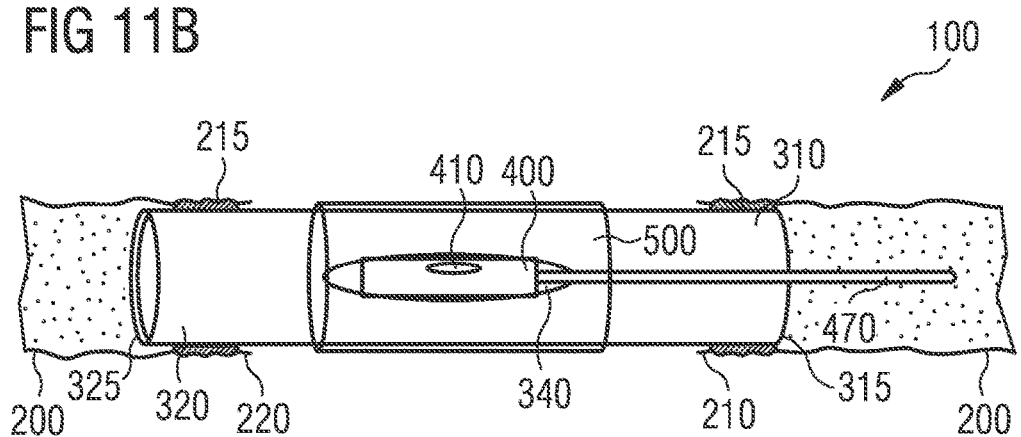
Figure 11C:
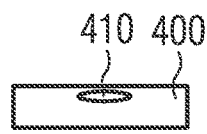
FIG. 11C is a schematic side view of a sensor unit of an implantable vessel fluid sensor of FIGS. 11A and 11B.

FIGS. 11A and 11B are a schematic view and a schematic top view of an implantable vessel fluid sensor 100 having a first end portion 310 and a second end portion 320 according to an embodiment. The second end portion 320 is extended from a second end 325, wherein the second end portion 320 shall be defined in an analogous way to the first end portion 310. Herein, FIG. 11C is a schematic side view of a sensor unit 400 of an implantable vessel fluid sensor 100 of FIGS. 11A and 11B.

According to this embodiment, the tubular body 300 includes, next to the first end portion 310, a second end portion 320. The second end portion 320 is configured to be inserted into and to form a sealed junction 215 with a remaining open vessel end 220 of the vessel 200 to form an artificial vessel part interconnecting the open vessel end 210 and the remaining open vessel end 220 of the vessel 200.

As shown in the embodiments of FIG. 2A to 10, a pressure sensor of the sensor unit 400 may be directly inserted into the vessel 200 to provide an optimum pressure solution and accuracy and solve the lifetime problem by recharging the battery in a short operation cycle via an inductive link. However, the vessel 200 that is used to insert the sensor unit 400 into the measurement position will be closed (similar to a catheter). This vessel 200 is typically a carotid artery of a mouse and this is only acceptable, since the carotid is available on the left and right side and the closure of one of both does not impact the mouse too much. However, it would be desirable to avoid the closure of the vessel and the blood flow would be an interesting additional information.

Thus, a bypass tube may be placed into the carotid or another vessel, wherein the bypass already contains at least one pressure sensor. Herein, the pressure sensor must not fit into the artery limiting the functionality and corresponding performance that can be implemented on the chip. Finally, the bypass solution adds freedom to design the cross-section of the blood flow path which enables the use of the Venturi-principle to extract the blood flow information from two pressure measurements. The described solutions will be presented with regard to the following Figures.

As shown in FIGS. 11A and 11B, the first end portion 310 is inserted into the open vessel end 210 to form a sealed junction 215 as described above with regard to FIG. 1A. The second end portion 320 is inserted into the remaining open vessel end 220 in a similar way as the first end portion 310 to form a sealed junction 215 in a similar way as the first end portion 310 and the open vessel end 210.

As shown in FIGS. 11A and 11B, the sensor unit 400 is connected to the transmission line 470 by the contact structure 402, wherein the transmission line 470 is fixed to the interconnection side 442 of the sensor unit 400 and the contact structure 402 is arranged at a sidewall and the sensor side 452 of the sensor unit 400, to be in contact with the sensor region 410 of the sensor unit 400. The structure of sensor unit 400 and transmission line 470 is inserted into the tubular body 300 through a cut, wherein the tube wall of the tubular body may elastically wrap around the sensor unit 400 and the transmission line 470. For inserting the sensor unit 400 into a cut or opening 340 of the tubular body 300, the tubular body 300 may be made of an elastic material such as silicone or a rubber material. The sensor unit 400 and the transmission line 470 may be supported by a patch or a wrist of microwire carrier foil to provide a sealing structure between the cut or opening 340 of the tubular body 300 and the sensor unit 400. The sensor unit 400 may be fixed and further sealed with a sealing structure 500, which may comprise a glue and/or a coating. In case the tube wall of the tubular body 300 comprise a rigid or stiff material, the tube wall needs a defined opening 340 that fits the shape of the sensor unit 400. The coating of the sealing structure 500 may comprise parylene, PTFE or silicone.

As can be seen from FIG. 11C, the sensor unit 400 comprises an interconnection side 442, wherein on the opposite sensor side 452, the active sensor area of the sensor region 410 is provided. The sensor unit 400 may comprise a silicon die or a semiconductor die. The active sensor area may be a MEMS-pressure semiconductor region as described above.

Figure 12A:
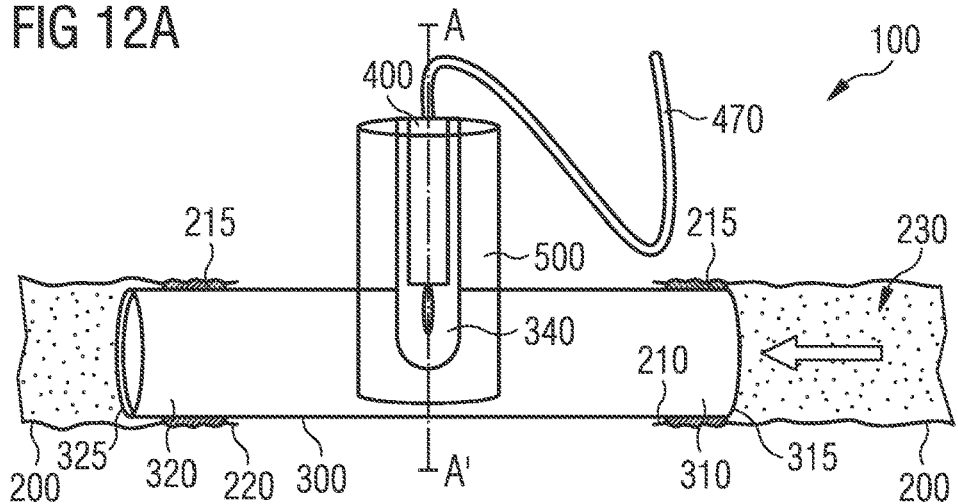
FIG. 12A is a schematic side view of an implantable vessel fluid sensor having a first end portion and a second end portion according to another embodiment.

FIG. 12A is a schematic side view of an implantable vessel fluid sensor 100 having a first end portion 310 and a second end portion 320 according to another embodiment.

As shown in FIG. 12A, the sensor unit 400 is inserted along its length direction (the direction, in which the transmission line 470 comprising a microwire is extended from the sensor unit 400) orthogonally into the tubular body 300. For inserting the sensor unit 400, as shown in FIG. 12A, into the tubular body 300, the part being opposite to the part, on which the transmission line 470 is fixed, may have a cone-shape, to facilitate the insertion of the sensor unit 400 into the tubular body 300.

Figure 12B:
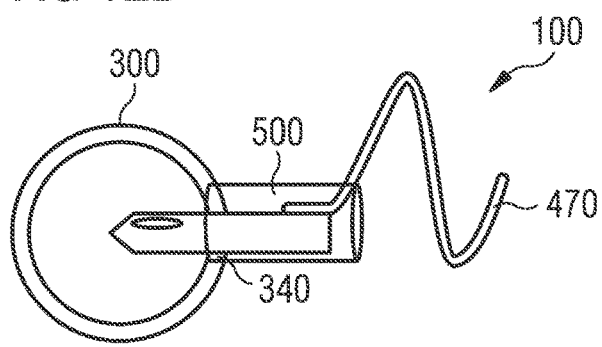
FIG. 12B is a schematic cross-sectional view of an implantable vessel fluid sensor taken along the section plane A-A' of FIG. 12A and having a sealing structure according to an embodiment.

As shown in FIG. 12B being a schematic cross-sectional view of the implantable vessel fluid sensor 100 taken along the section plane A-A' of FIG. 12A, the sensor unit 400 is just partly inside the tubular body 300, wherein the sensor region 410 is inside the tubular body 300 to be in direct contact with the vessel fluid 230, and the fixing part of the transmission line 470 is outside the tubular body 300 and sealed and fixed to the outer wall of the tubular body 300 by a sealing structure 500 such as a glue or a coating. The shaping of the sensor unit 400 inside of the tubular body 300 may be optimized to reduce turbulence within the stream of the vessel fluid 230 in the tubular body 300. In addition, the front side of the sensor unit 400 being opposite to the fixing side of the transmission line 470 may be optimized (e.g. a cone-shape) to make it easy to insert the chip of the sensor unit 400 into the flexible tubular body. Herein, the tubular body 300 may comprise silicone or another flexible material.

Figure 12C:
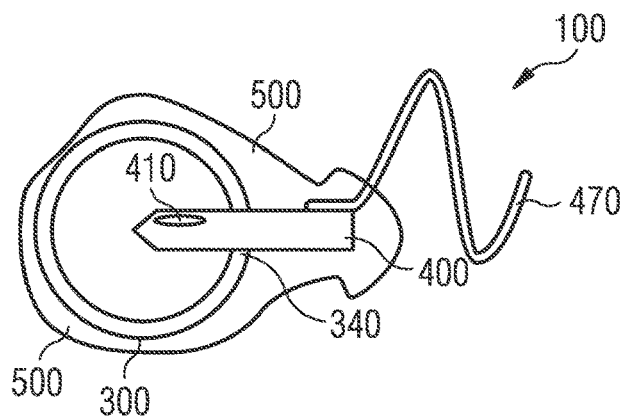
FIG. 12C is a schematic cross-sectional view of an implantable vessel fluid sensor taken along the section plane A-A' of FIG. 12A and having a sealing structure according to another embodiment.

As shown in FIG. 12C, an additional sealing structure 500 enclosing the complete sensor unit 400 and the tubular body 300 may be provided.

FIG. 13A is a schematic side view of an implantable vessel fluid sensor 100 having a first end portion 310 and a second end portion 320 and including a T-tube according to another embodiment.

Herein, the sensor region 410 of the sensor unit 400 is inserted in a cut or an opening 340 for the tubular body 300, wherein the cut or the opening 340 is sealed by a sealing structure 500.

As shown in FIG. 13A, the tubular body 300 includes a T-tube having a first end portion 310 and a second end portion 320, and further having a sensor end portion 350 for accommodating the sensor unit 400. Herein, the sensor end portion 350 has a blind end 352. The blind end 352 may be formed by a sealing structure 500.

The structure of the sensor unit 400 as shown in FIGS. 13B and 13A is comparable to the structure of the sensor unit 400 as shown in FIG. 11A to 11C. The sensor region 410 of the sensor unit 400 may be arranged closely to the inside of the tubular body 300. The sensor region of the sensor unit 400 may be arranged at most in a range of two-times to five-times the outer diameter of the tubular body 300 to the inner volume of the tubular body 300 arranged between the first end portion 310 and the second end portion 320.

The blind end 352 avoids reduction of the blood flow cross-section and turbulence of the vessel fluid stream inside the tubular body 300 between the first end portion 310 and the second end portion 320. The sealing is simplified by filling a part of the sensor end portion 350 with synthetic material to form a seal or a glue plug. The sealing 500 can fix the silicon die or the sensor unit 400 position as well inside the sensor end portion 350.

Figure 14:
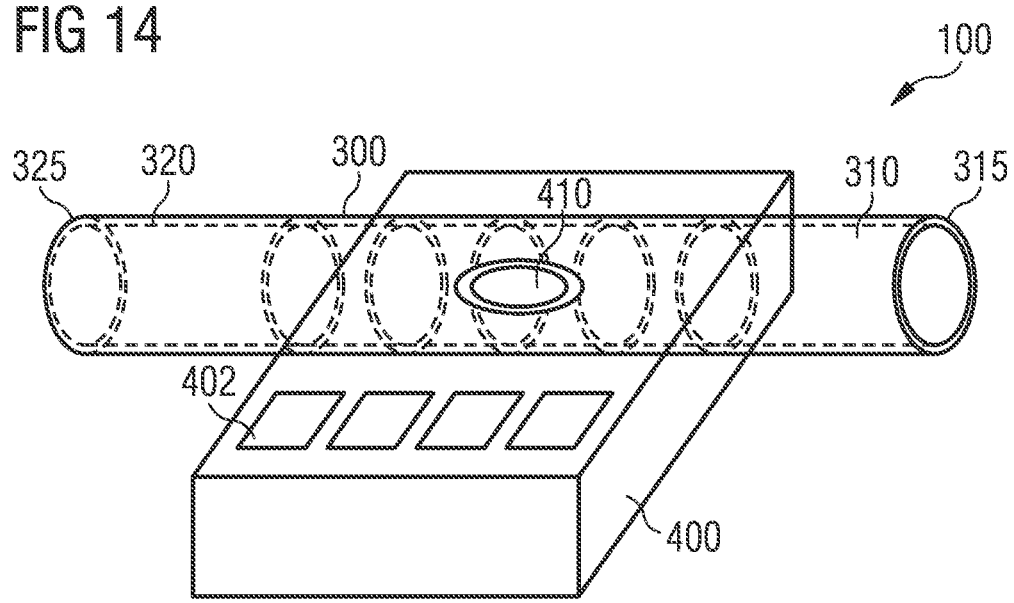
FIG. 14 is a schematic perspective view of an implantable vessel fluid sensor having a first end portion and a second end portion and having a sensor unit backpacked on a tubular body according to an embodiment.

FIG. 14 is a schematic perspective view of an implantable vessel fluid sensor 100 having a first end portion 310 and a second end portion 320 and having a sensor unit 400 being backpacked on the tubular body 300 according to an embodiment.

Herein, the tubular body 300 is attached to the sensor unit 400 and has a sensor opening 360 at the sensor region 410 of the sensor unit 400. The area of the attached tubular body 300 is smaller than the area of the sensor unit 400 facing the tubular body 300.

Figure 15A:
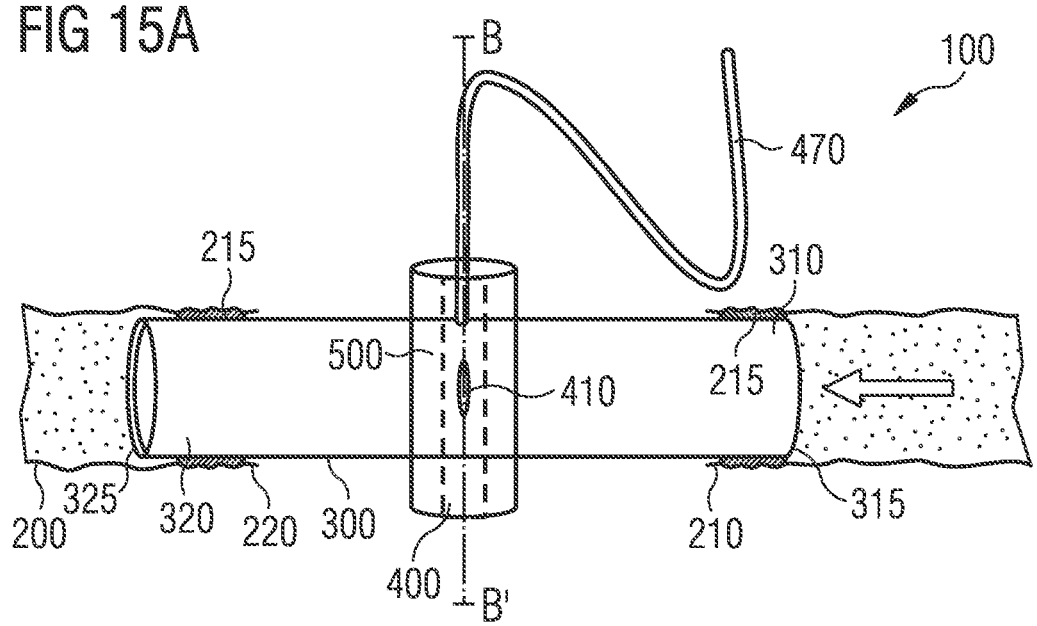
FIG. 15A is a schematic side view of an implantable vessel fluid sensor having a first end portion and a second end portion and having a sensor unit backpacked on a tubular body according to an embodiment.
Figure 15B:
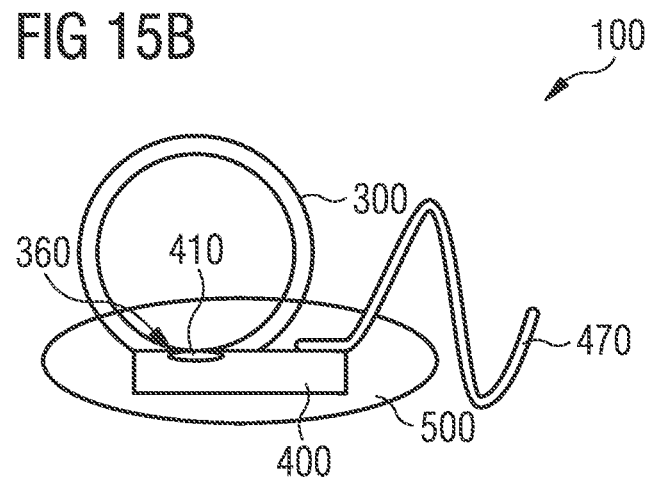
FIG. 15B is a schematic cross-sectional view of an implantable vessel fluid taken along the section plane B-B' of FIG. 15A.

In other words, the chip of the sensor unit 400 is larger than the tube of the tubular body 300 and overlaps the tubular body 300. Herein, at least the sensor region 410 of the sensor unit 400 is inside the tubular body 300. Electrical contacts of the contact structure 402 for contacting the microwire of the transmission line 470 may be kept outside for facilitating the sealing. The sensor unit 400 may be completely sealed by a sealing structure 500, as can be seen in FIG. 15B. As further shown in FIG. 15A, the sensor unit 400 may be arranged orthogonally to the tubular body 300, wherein the length direction of the sensor unit 400 is the direction, in which the transmission line 470 is extended from the sensor unit 400.

For forming the sensor opening 360 as shown in FIG. 15B, the tube walls of the tubular body 300 may be made of a stiff material such as glass, wherein the sensor opening 360 in the tubular body 300 may be formed by mechanically abrasing a part of the tubular wall of the tubular body 300 to form the sensor opening 360. In addition, in case the tubular body 300 comprises a flexible material, the tube wall of the tubular body 300 may be easily cut out and the tubular wall of the tubular body 300 facing the sensor unit 400 may be glued to the sensor side 452 of the sensor unit 400, on which the sensor region 410 is arranged, by a glue such as a silicone glue. By providing this back-pack-approach, the chip may be much larger as the diameter of the tubular body 300, thus, the sensor unit 400 may have also a processing unit or a communication unit for converting the analogue pressure signal sensed by the sensor region 410. Thus, also an optical communication unit may be integrated in the sensor unit 400 to transmit the sensor information to the external device 600 via an optical fibre. Thus, the transmission line 470 may also be an optical fibre for transmitting sensor information.

Figure 16:
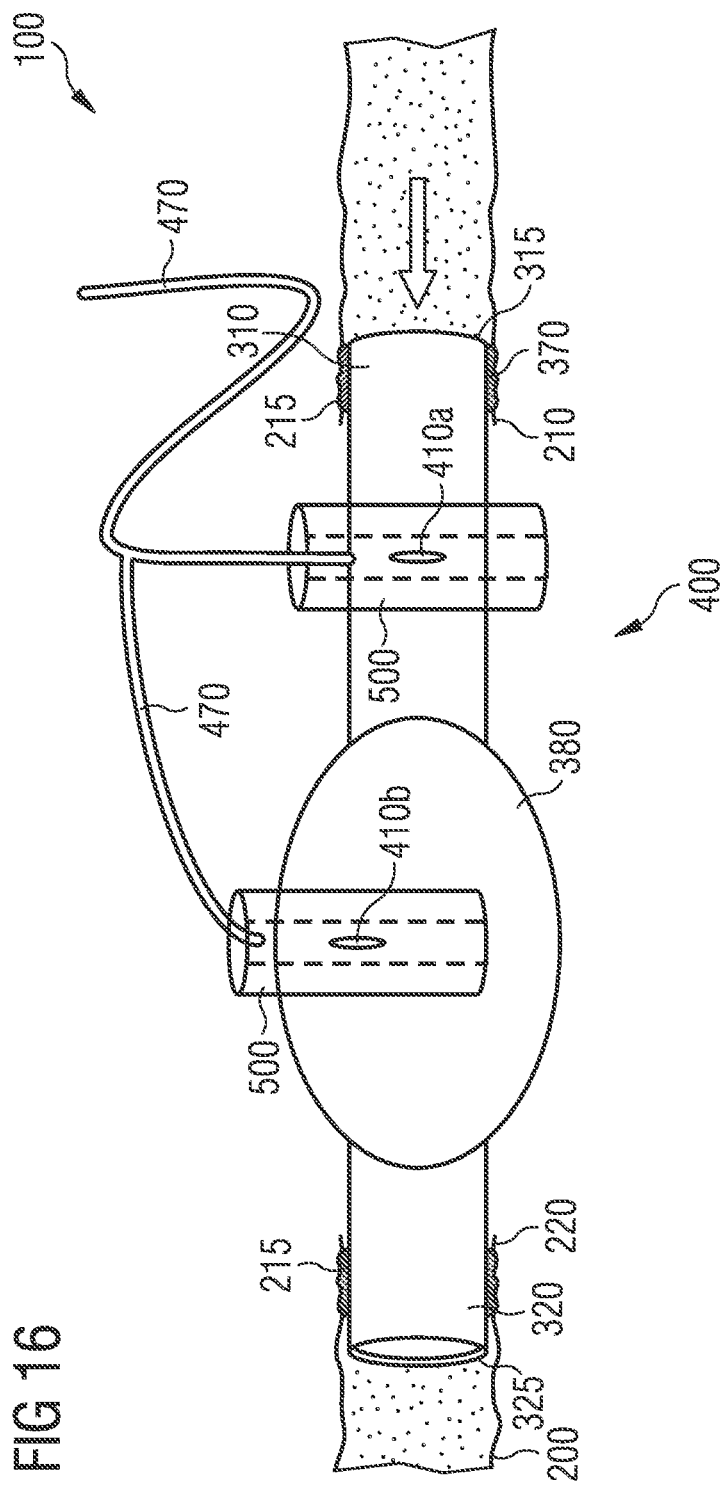
FIG. 16 is a schematic perspective view of an implantable vessel fluid sensor having a first end portion and a second end portion and having tubular body parts with different cross-sectional areas according to an embodiment.

FIG. 16 is a schematic perspective view of an implantable vessel fluid sensor 100 having a first end portion 310 and a second end portion 320 and having tubular body parts with different-cross-sectional areas $A_1$, $A_2$ according to an embodiment. As shown in FIG. 16, the tubular body 300 comprises a first part 370 having a first cross-sectional area $A_1$ and a second part 380 having a second cross-sectional area $A_2$. The second cross-sectional area $A_2$ is different to the first cross-sectional area $A_1$. The sensor unit 400 comprises a first sensor region 410*a* sensing the fluid pressure at the first part 370, and a second sensor region 410*b* sensing the fluid pressure at the second part 380.

Thus, the vessel fluid flow may be measured as follows. According to the flow continuity rule:

$$v_1 A_1 = v_2 A_2,\qquad\text{Equation (1)}$$

wherein $v_1$ is the vessel fluid flow velocity in the first area $A_1$, and $v_2$ is the vessel fluid flow velocity in the second area $A_2$. Due to conservation of energy (Venturi effect):

$$p_1 - p_2 = \rho/2(v_1^2 - v_2^2),\qquad\text{Equation (2)}$$

wherein $p_1$ is the pressure within the first part 370 and $p_2$ is the pressure in the second part 380, $\rho$ is the density of the vessel fluid 230.

Thus, by measuring the cross-sectional areas $A_1$, $A_2$ and the pressure difference $p_1-p_2$, the velocity $v_1$ may be determined by substituting the two above equations:

$$v_1 = \sqrt{(2(p_1-p_2)/(1-A_1^2/A_2^2))}\qquad\text{Equation (3)}$$

Thus, by using the Venturi effect and by knowing the cross-sectional areas, the blood flow velocity may be calculated from the pressure difference $p_1-p_2$ while having predetermined cross-sectional areas of the first part 370 being $A_1$ and the second part 380 being $A_2$.

The sensor structure as shown FIG. 16 may further be combined with further sensor units 400 for measuring different blood vessel fluid parameters. The sensor units 400 as shown in FIG. 16 may be arranged with regard to the tubular body 300 according to the embodiments as shown in FIG. 11A to 15B, wherein the backpack-principle may be advantageous since no turbulences are generated in the flow direction of the vessel fluid 230 between the first end portion 310 and the second end portion 320.

Thus, the structure of FIG. 16 can be combined with all previously suggested chip embedding principles. The bypass channel between the first end portion 310 and the second end portion 320 has, as shown in FIG. 16, a widened cavity with the second sensor region 410b. However, the widened cavity may be also be arranged at the first part 370.

Figure 17:
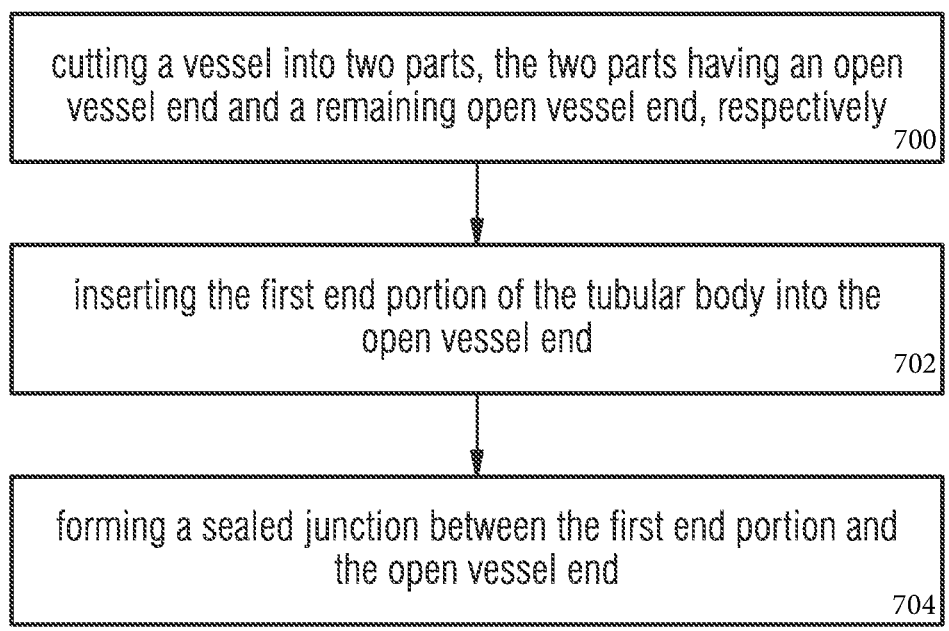
FIG. 17 is a flow chart illustrating a method of implanting an implantable vessel fluid sensor according to an embodiment.

FIG. 17 is a flowchart illustrating a method of implanting an implantable vessel fluid sensor 100 according to an embodiment.

According to an embodiment, a method of implanting an implantable vessel fluid sensor 100 as described above may comprise the following steps. First of all, a vessel 200 is cut into two parts, wherein the two parts have an open vessel end 210 and a remaining open vessel end 220, respectively (Block 700). Thereafter, the first end portion 310 of the tubular body 300 is inserted into the open vessel end 210 (Block 702). Then, a sealed junction 215 is formed between the first end portion 310 and the open vessel end 210 (Block 704). The sealed junction 215 may be formed by clamping, by suture, or by tying, wherein all usual surgical method for forming a sealed junction between a bypass part and an open vessel end shall be included.

In case an implantable vessel fluid sensor 100 as shown in FIG. 2A to 10 may be implanted in the open vessel end 210, the remaining open vessel end 220 may be closed by sclerotherapy or any other suitable surgical method for closing an open vessel end.

In case an implantable vessel fluid sensor 100 as shown in FIG. 11A to 16 is implanted in the vessel 200 to form a bypass or an artificial vessel part interconnecting the open vessel end 210 and the remaining open vessel end 220 of the vessel 200, the second end portion 320 of the tubular body 300 may be inserted into the remaining open vessel end 220. Thereafter, a sealed junction 215 between the second end portion 320 and the remaining open vessel end 220 may be formed by clamping, by suture or by tying, as described above.

According to the embodiments of FIG. 11A to FIG. 16, it is avoided to close the vessel 200 with the complete silicon die of the sensor unit 400 as shown in FIG. 2A to 10. Herein, the sensors of the sensor unit 400 are located in a cut or opening of the tube wall of the tubular body 300. The material could be stiff or flexible (glass, PET, PI, silicone) or combined (e.g. glass center with silicone extensions). Ports of the tubular body 300 (the first end portion 310 and the second end portion 320) may be connected to the vessel 200. The glue may be a synthetic glue.

Thus, as described above, an implantable vessel fluid sensor 100 is provided, which facilitates the implanting into a vessel, which may be a blood vessel or carotid artery of a rodent such as a mouse to provide accurate measurement results. The accurate measurement results result from the small distance of the sensor region 410 of the sensor unit 400 being in direct contact with the vessel fluid 230 and to the natural environment inside the vessel 200. Thus, the sensor region 410 is either implanted directly within the vessel 200 or the distance between the open vessel end 210 and the sensor region 410 is at least ten-times the outer diameter of the tubular body 300, leading to an excellent aspect ratio between the cross-sectional area of the vessel fluid flow (having a comparable size to the outer diameter of the tubular body) and the location of the sensor region 410 of the sensor unit 400 in the vessel fluid flow of the vessel 200.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An implantable vessel fluid sensor configured to sense at least one vessel fluid parameter of a vessel, the implantable vessel fluid sensor comprising:
   a tubular body including a first end portion and a second end portion and forming an open channel between the first end portion and the second end portion, the first end portion being configured to be inserted into and to form a sealed junction with a first open vessel end of the vessel, the second end portion being configured to be inserted into and to form a sealed junction with a second open vessel end of the vessel to form an artificial vessel part interconnecting the first open vessel end and the second open vessel end of the vessel; and
   a semiconductor sensor unit connected to the open channel of the tubular body and comprising a semiconductor sensor region configured to be in direct contact with a vessel fluid in a sealed junction state.

2. The implantable vessel fluid sensor of claim 1, wherein the semiconductor sensor region of the semiconductor sensor unit is inserted in a cut or an opening of the tubular body, and wherein the cut or the opening is sealed by a sealing structure.

3. The implantable vessel fluid sensor of claim 1, wherein the tubular body includes a T-tube having the first end portion and the second end portion, and further having a sensor end portion for accommodating the semiconductor sensor unit, the sensor end portion having a blind end.

4. The implantable vessel fluid sensor of claim 1, wherein the tubular body is attached to the semiconductor sensor unit and has a sensor opening at the semiconductor sensor region of the semiconductor sensor unit, the area of the attached tubular body being smaller than the area of the semiconductor sensor unit facing the tubular body.

5. The implantable vessel fluid sensor of claim 1, wherein the tubular body comprises a first part having a first cross-sectional area and a second part having a second cross-sectional area, the second cross-sectional area being different than the first cross-sectional area, and wherein the semiconductor sensor unit comprises a first semiconductor sensor region configured to sense fluid pressure at the first part and a second semiconductor sensor region configured to sense the fluid pressure at the second part.

6. A method of implanting an implantable vessel fluid sensor, the method comprising:
   providing an implantable vessel fluid sensor configured to sense at least one vessel fluid parameter of a vessel, the implantable vessel fluid sensor comprising: a tubular body including a first end portion, the first end portion being configured to be inserted into and to form a sealed junction with an open vessel end of the vessel; and a sensor unit connected to the tubular body and comprising a sensor region configured to be in direct contact with a vessel fluid in a sealed junction state, wherein a minimum distance between the sensor region and the first end portion is at most 10 times an outer diameter of the first end portion of the tubular body, and wherein the sensor unit is a semiconductor device comprising: a proximal part plugging the first end portion of the tubular body and having an interconnection side; and a distal part protruding from the first end portion of the tubular body and having a sensor side
   cutting a vessel into two parts, the two parts having an open vessel end and a remaining open vessel end, respectively;
   inserting the first end portion of the tubular body into the open vessel end; and
   forming a sealed junction between the first end portion and the open vessel end.

* * * * *